United States Patent [19]
Hively

[11] 3,944,963
[45] Mar. 16, 1976

[54] METHOD AND APPARATUS FOR ULTRASONICALLY MEASURING DEVIATION FROM STRAIGHTNESS, OR WALL CURVATURE OR AXIAL CURVATURE, OF AN ELONGATED MEMBER

[75] Inventor: Lee Mizener Hively, Williamsport, Pa.

[73] Assignee: Western Electric Co., Inc., New York, N.Y.

[22] Filed: Aug. 21, 1974

[21] Appl. No.: 499,378

[52] U.S. Cl. ............................... 340/1 R; 73/67.8 R
[51] Int. Cl.² ...................... G01S 9/66; G01N 29/00
[58] Field of Search............ 340/1 R; 33/1 P, 174 L, 33/174 P, 178 E; 73/67.7, 67.8 R

[56] References Cited
UNITED STATES PATENTS

| | | | |
|---|---|---|---|
| 2,629,082 | 2/1953 | Hare | 340/1 R |
| 2,640,190 | 5/1953 | Rines | 340/1 R |
| 2,801,403 | 7/1957 | Kietz | 340/1 R |
| 3,380,293 | 4/1968 | Murphy | 73/67.7 |
| 3,577,773 | 5/1971 | Kubo et al. | 73/67.7 |
| 3,820,387 | 6/1974 | Grabendorfer et al. | 73/67.9 |

*Primary Examiner*—Richard A. Farley
*Attorney, Agent, or Firm*—E. W. Pfeifle

[57] ABSTRACT

Apparatus for measuring deviation from straightness, or wall curvature or axial curvature, of an elongated member by ultrasonic pulse-echo techniques comprises at least three ultrasonic transducer means and an associated processing system.

In operation, each of the transducer means transmits ultrasonic search signals towards the elongated member and detects signals reflected from diametrically opposed points on a reference surface of the member. From the transmitted search and the received echo signals, a signal is generated in the associated processing system indicating the distance between the face of each transducer means and the associated reference points on the wall surface of the elongated member. The generated distance signals can then be processed to generate signals indicating wall curvature and axial curvature in the plane formed by the diametrically opposed points.

10 Claims, 7 Drawing Figures

METHOD AND APPARATUS FOR ULTRASONICALLY MEASURING DEVIATION FROM STRAIGHTNESS, OR WALL CURVATURE OR AXIAL CURVATURE, OF AN ELONGATED MEMBER

BACKGROUND OF THE INVENTION

1. Field of the Invention

This invention relates to a method and apparatus for measuring deviation from straightness, or wall curvature or axial curvature, of an elongated member, such as, for example, a tube, using ultrasonic pulse-echo techniques.

2. Description of the Prior Art

A wide variety of ultrasonic testing and measuring systems exist which are capable of either inspecting materials or workpieces for hidden flaws, or gauging the thickness or diameter of a workpiece. Typically, in ultrasonic pulse-echo apparatus, an electronic pulse generator provides pulses to an ultrasonic transducer acoustically coupled to the surface of the material or workpiece. In response to the electrical signal from the pulse generator, the transducer transmits a search signal which propagates through the coupling medium and into the workpiece. When an acoustic discontinuity, as for example, a flaw, lamination, or wall surface, is encountered in the workpiece by the search signal, a reflection or echo signal is produced which is detected by the transducer and converted into an electrical echo signal. The electrical search and echo signals from the transducer are generally used either to respectively trigger and stop a clock circuit or to provide a coordinate display on a cathode ray tube. From the time elapsed between the transmission of a search signal and the receipt of an echo signal by the transducer, it is possible to determine the distance between the face of the transducer and the acoustic discontinuity represented by the flaw, lamination or wall surface of the workpiece. A typical prior art system for measuring the thickness and location of a flaw in a workpiece, as described above, is found in U.S. Pat. No. 3,570,279, issued to D. H. Davies on Mar. 16, 1971.

U.S. Pat. No. 3,780,442, issued to W. M. Gresho on Dec. 25, 1973 discloses measuring the axial curvature of an elongated member, such as, for example, a tube. A plurality of wall curvature gauges are both mounted independent of each other on a rigid carrier and arrayed equiangularly about the axis of the carrier to form a compound gauge. Each curvature gauge comprises a subcarrier having a radially movable probe mounted on the subcarrier between two radially extending, spaced apart, fixed feet, and a linear variable differential transformer (LVDT) coupled to the probe. When the gauge is positioned in the tube, the tips of the fixed feet contact the referenced surface of the tube to form a longitudinal reference line therebetween. Any deviation from the reference line by the tip of the probe, which is in contact with the referenced surface of the tube, will cause the associated LVDT to generate a corresponding electrical signal thereby to indicate wall curvature along a particular wall area. Each of the LVDT generated electrical signals are proportionately weighted and concurrently processed to provide a single continuous output voltage signal indicating the axial curvature of the tube. The Gresho patent, however, does not disclose nor teach non-contact method of apparatus, or the use of ultrasonic pulse-echo techniques for effecting an axial curvature measurement of an elongated member.

The problem, therefore, is to provide method and apparatus which will measure the axial curvature of an elongated member while avoiding contact of the measuring apparatus with a surface of the member.

BRIEF SUMMARY OF THE INVENTION

An object of the present invention is to provide new and improved method and apparatus for measuring the wall curvature and the axial curvature of an elongated member such as, for example, a tube by the use of ultrasonic pulse-echo techniques.

Other and further objects of the present invention will become apparent during the course of the following description and by reference to the accompanying drawings and the appended claims.

In accordance with the present invention, the method for measuring the deviation from straightness between two points along one surface of a member comprises the steps of reflecting ultrasonic signals off said surface along paths approximately normal thereto from sites respectively opposite said two points and one point intermediate said two points, said sites being nominally equidistant from said surface and at predetermined distances from one another; generating first electrical signals representing the transit times of said reflected ultrasonic signals; and generating a second electrical signal in response to the generation of said first signals indicative of the deviation from straightness of said surface between said two points.

In an alternative embodiment, axial curvature of the elongated member is measured in the plane of said paths by similarly measuring the deviation from straightness along a second surface of said member, or a second portion of said one surface symmetric about the longitudinal axis of said member, and on the opposite side of the longitudinal axis of said member from said one surface; and then generating a third electrical signal in response to the second electrical signals associated with both said one surface and said second surface or second portion of said one surface indicative of said axial curvature.

BRIEF DESCRIPTION OF THE DRAWINGS

Referring now to the drawings, in which like numerals represent like parts in the several views.

DESCRIPTION OF THE PREFERRED EMBODIMENTS

Figure 1:
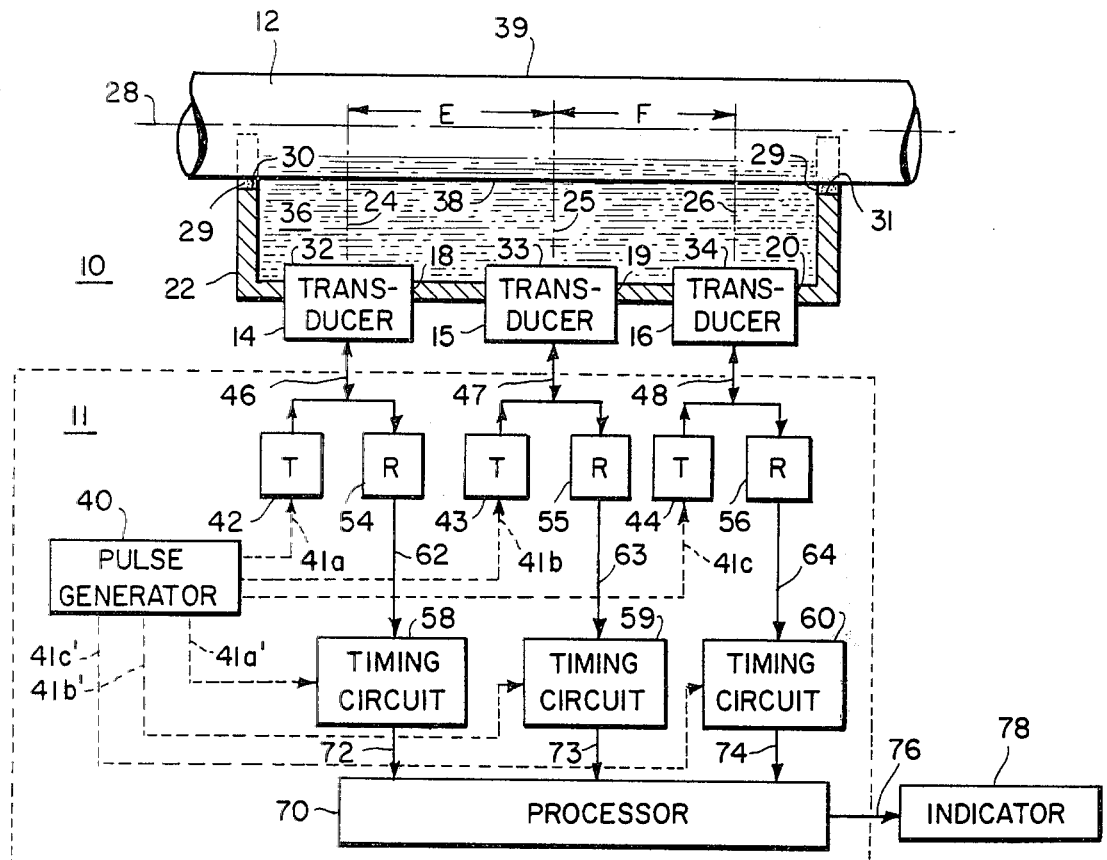
FIG. 1 is a block diagram of a nondestructive ultrasonic axial curvature measuring system embodying one form of the present invention.

In FIG. 1, a block diagram of a system, designated generally as 10, capable of measuring both the wall curvature and axial curvature of a solid cylindrical elongated member 12 by ultrasonic pulse-echo techniques is illustrated. Member 12, while typically a right circular cylinder, may have any shape, e.g., elliptical, square, triangular, etc., and may be hollow, as will be discussed hereinafter with reference to FIGS. 4 to 7. It will, of course, be understood that the elongated member 12 to be tested is formed from an acoustical transmitting material such as, for example, steel.

As shown in FIG. 1, system 10 comprises three, spaced-apart, ultrasonic transducers 14–16 in a noncontacting arrangement with the wall surface of elongated member 12, and a processing system 11 capable of exciting transducers 14–16 to emit ultrasonic waves and processing information relative to reflected waves received by transducers 14–16 thereby to determine wall curvature and axial curvature at a portion of member 12. As will be explained hereinafter with reference to FIGS. 5–7, the present invention may also be practiced using more than three transducers.

Transducers 14–16 are shown mounted in, and extending through, apertures 18–20, respectively, in the bottom of a tank 22, such that the longitudinal axes 24-26 of transducers 14–16, respectively, are arranged approximately normal to the longitudinal axis 28 of member 12 to define a plane which includes approximately the longitudinal axis 28 of member 12 when said member 12 is positioned in cut-outs 30, 31 formed in the ends of tank 22. Furthermore, the faces 32–34 of transducers 14–16, respectively, are preferably aligned to define a plane which is approximately parallel with the longitudinal axis 28 of member 12 when said member 12 is positioned in cut-outs 30,31.

Since transducers 14–16 are not in contact with the wall surface of member 12, a suitable acoustic coupling medium 36, e.g., oil, water, etc., is placed in tank 22 between elongated member 12 and the faces 32–34 of transducers 14–16, respectively, to permit acoustic energy pulses to propagate therebetween as is well known to those familiar with the art.

Cut-outs 30,31, in tank 22, correspond in shape to the outer wall surface of member 12 but are slightly larger and comprise a rubber glanding system 29, known in the art, around the entire lip of said cut-outs 30 and 31 thereby to contact said outer wall surface of member 12 and form a bearing with said outer wall surface which substantially prevents leakage of the coupling medium 36 from tank 22 during the measuring process. Cut-outs 30,31 also provide support for member 12 at two relatively closely spaced locations thereby to substantially eliminate sag, and a possible error in wall curvature or axial curvature measurements when member 12 is undergoing measurement. It is preferable to support member 12 at a plurality of points on either side of tank 22 by any suitable conveying means (not shown but known to those familiar with the art), such as, for example, supporting rollers. The conveying means would reduce any tendency for member 12 to bend under its own weight and thereby affect a curvature measurement.

In processing system 11, a pulse generator 40, capable of producing a series of intermittently occurring high frequency pulses, is connected via cables 41a–41c to transmitters 42–44, respectively, each transmitter being associated with a separate one of the transducers 14–16, respectively. Transmitters 42–44 may be of an essentially conventional type capable of producing driving signals suitable for exciting transducers 14–16, respectively, into radiating ultrasonic energy search pulses in response to individual electrical pulses over cables 41a–41c from pulse generator 40. As is known in the art, a pulse, from pulse generator 40, capable of exciting an individual transducer into radiating energy, can be characterized by a relatively high voltage, e.g., 200–250 volts, and a very fast rise time. Therefore, it is preferable to provide pulses in a cyclical manner to each of transmitters 42–44 with gating circuits (not shown) that can be provided as part of pulse generator 40 or separately within the areas of cables 41a–41c. Alternatively, a separate pulse generator (not shown) can be connected to each of transmitters 42–44. Furthermore, by properly timing the cyclical pulses to transmitters 42–44 and the respective transducers 14–16, it is possible to prevent pulse energy reflected from the wall surfaces 38 and 39 of member 12, from affecting measurements at each of the other transducers. The individual high frequency pulses from pulse generator 40 are transmitted from transmitters 42-44 to transducers 14–16, respectively, over respective cables 46–48. Transducers 14–16, excited by the high frequency pulses, emit corresponding search pulses of ultrasonic energy toward elongated member 12 through coupling medium 36.

Figures 2, 3:
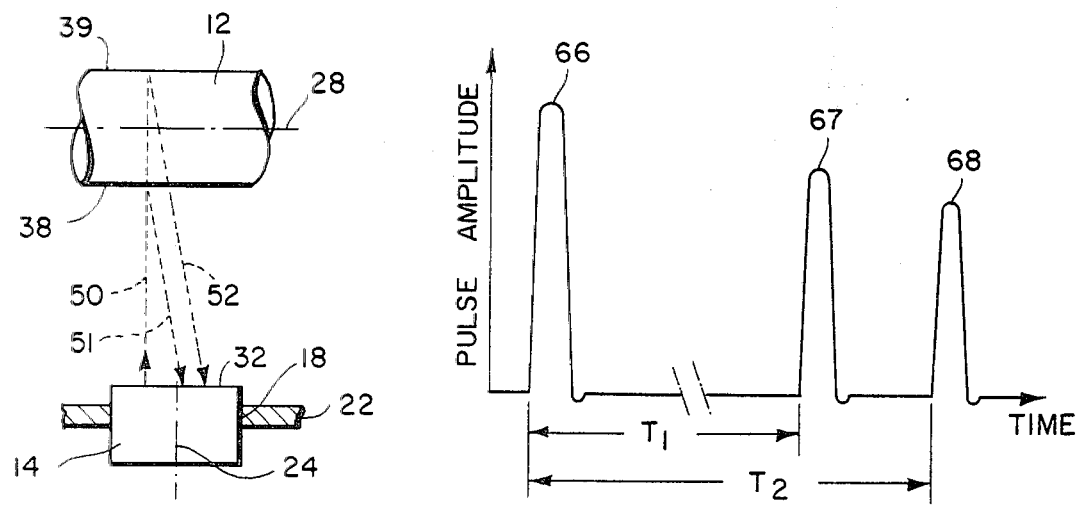
FIG. 2 is a diagram showing the principle of the reflection-type ultrasonic measuring apparatus forming part of the measuring system of FIG. 1 when measuring a solid elongated member.
FIG. 3 is a schematic representation of an ultrasonic pulse train including reflections from wall surfaces of a solid elongated member as shown in FIG. 2.

As shown in FIG. 2 for typical transducer 14, each search pulse of ultrasonic energy from the face 32 of transducer 14 propagates through coupling medium 36 normal to the surface of member 12 along a path 50. On reaching the external wall surface 38 of member 12 nearest transducer 14, a portion of the transmitted ultrasonic pulse energy is reflected from said nearest surface 38 of member 12 perpendicularly back towards the face 32 of transducer 14 along a path 51, the remainder of the pulse energy continuing through member 12 along path 50. On reaching the external wall surface 39 of member 12 furthest from transducer 14 and diametrically opposed to said nearest wall surface 38, the remaining ultrasonic pulse energy is reflected from said furthest wall surface 39 perpendicularly back towards the face 32 of transducer 14 along a path 52. Paths 50, 51 and 52 are substantially aligned with one another, but are shown separated in FIG. 2 for purposes of explanation. It is known to those skilled in the art that successive reflections occur between the wall surfaces 38 and 39 of member 12 and shown as dotted lines in FIG. 2. These successive reflections, however, are not pertinent for practicing the present invention and will not be included in the discussions of FIGS. 2 and 3.

The reflected energy, in the form of echoes, from the diametrically opposed wall surfaces 38 and 39 of member 12, resulting from each of the simultaneously transmitted ultrasonic search pulses from transducers 14-16, is received by the associated transducer and converted to a corresponding electrical output signal. The individual electrical output signals from transducers 14–16 are transmitted over cables 46–48, respectively, to respective receivers 54–56. Receivers 54–56 are shown in block form in FIG. 1 and can be of any conventional type known in the art, the receivers 54–56 generally having an amplifier for amplifying the electrical output signal from transducers 14–16, respectively. Receivers 54–56 each supply an output signal over cables 62–64, respectively, to respective timing circuits 58–60.

Timing circuits 58–60 are also connected via cables 41a'–41c', respectively, to pulse generator 40 and gating circuits (not shown) in said pulse generator 40 or in cables 41a'–41c', to receive the pulses from generator 40 as said pulses are supplied to the associated transmitters 42–44 and in turn to transducers 14–16, respectively. The search pulses generated by each of transducers 14–16 in response to both a pulse from the associated transmitter 42–44, respectively, and the pulse energy reflected from the diametrically opposed wall surfaces 38 and 39 of member 12, if displayed on a cathode ray tube, instead of being received by timing circuits 58–60, would appear as shown in FIG. 3. In FIG. 3, pulse 66 represents the pulse from pulse generator 40 as said pulse arrives at each of the transducers, e.g., transducer 14. The energy radiating from each transducer 14–16 in response to pulse 66 is that energy which propagates along path 50 in FIG. 2. Pulses 67 and 68 of FIG. 3 represent the pulses generated by each of the transducers 14–16 in response to the detected pulse energy reflected from the nearest and furthest wall surfaces 38 and 39, respectively, of member 12 and propagating along respective paths 51 and 52 as shown in FIG. 2.

Timing circuits 58–60 are shown in block form in FIG. 1 and can be of any conventional type known in the art. Timing circuits 58–60 produce an output signal indicating the time elapsed between the initiation of a transmitted search pulse 66 (FIG. 3) from the associated transducer 14–16, respectively, and the receipt of any reflected wave, e.g., pulses 67 and 68 of FIG. 3, by the associated transducer 14–16. For example, each timing circuit 58–60 of FIG. 1 provides an output signal indicating the time elapsed between pulses 66 and 67 of FIG. 3, designated as elapsed time T1, and pulses 66 and 68 of FIG. 3, designated as elapsed time T2. Timing circuits 58–60 can attain such time measurements either by producing separate signals indicating the time elapsed between search pulse 66 and each of pulses 67 and 68 of FIG. 3 (designated as T1 and T2, respectively), or by producing a first signal indicating the time elapsed between pulses 66 and 67 (T1) and then producing a second signal indicating the time elapsed between pulses 67 and 68, which can be added to said first signal (T1) to arrive at the elapsed time between pulses 66 and 68 (T2).

The individual output signals from timing circuits 58–60 are received by a processor 70 over cables 72–74, respectively. Processor 70, in turn, is adapted to generate a signal indicating the distance between each of the faces 32–34 of transducers 14–16, respectively, and each of the diametrically opposed wall surfaces 38 and 39 of member 12 using the known sonic propagation velocities of the coupling medium 36 and the material of member 12.

Processor 70 is also adapted to generate a signal indicating the deviation from straightness, corresponding to longitudinal wall curvature, of a particular one or both of the diametrically opposed wall surfaces 38 and 39 of member 12, in accordance with any well-known trigonometric technique. For example, having determined the distance actually measured between the face 32 of transducer 14 and the point on the nearest wall surface 38 of member 12 intersecting longitudinal axis 24 of transducer 14 (designated hereinafter as distance $y_{14}$) and the distance actually measured between the face 34 of transducer 16 and the point on the nearest wall surface 38 of member 12 intersecting longitudinal axis 26 of transducer 16 (designated hereinafter as distance $y_{16}$), it is possible to compute the theoretical distance ($y'_{15}$) between the face 33 of transducer 15 and the point on longitudinal axis 25 of transducer 15 where the nearest wall surface 38 of member 12 would intersect longitudinal axis 25 if said wall surface 38 were perfectly straight using the equation $$y'_{15} = y_{14} + (y_{16} - y_{14}) \left( \frac{E}{E+F} \right) \qquad (1)$$

where
$E$ = the distance between longitudinal axes 24 and 25 of transducers 14 and 15, respectively, (see FIG. 1), and
$F$ = the distance between longitudinal axes 25 and 26 of transducers 15 and 16, respectively, (see FIG. 1).

The difference between the predicted distance $y'_{15}$ and the distance $y_{15}$ actually measured between the face 33 of transducer 15 and the point where the nearest surface 38 of member 12 intersects longitudinal axis 25 of transducer 15 can then be determined to arrive at the magnitude of the deviation from straightness ($h_1$), where $h_1 = y'_{15} - y_{15}$, of said nearest wall surface 38. The radius of curvature ($R_1$) of the wall surface 38 nearest transducers 14–16 can then be determined from the equation $$R_1 = (E)(F)/2h_1 \qquad (2)$$

The magnitude of the deviation from straightness ($h_2$) and the radius of curvature ($R_2$) for the wall surface 39 of member 12 diametrically opposed to said wall surface 38 nearest transducers 14–16 can also be determined in a similar manner. The axial curvature of said elongated member 12 in the plane defined by the two diametrically opposed wall surfaces can then be found using the equation $$R_{c1} = (E)(F)/(h_1 + h_2) \qquad (3)$$

To completely define the radius of curvature in elongated member 12 in accordance with the above procedure, the axial curvature ($R_{C2}$) in a second plane approximately normal to the first plane just measured should be measured in a manner similar to that described hereinabove for said first plane. The net radius of curvature (R) for elongated member 12 along longitudinal axis 28 can be determined by the equation $$R = \sqrt{R_{c1}^2 + R_{c2}^2} \qquad (4)$$

Figure 4:
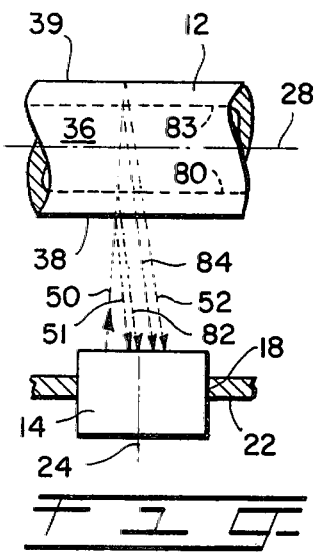
FIG. 4 is a diagram showing the principle of a reflection-type ultrasonic measuring apparatus forming part of the measuring system of FIG. 1 when measuring a hollow member filled with an acoustic transmitting medium.

The output signal from processor 70 is transmitted over cable 76 to an indicator 78 which can be any of the conventional visual or recording indicators known in the art.

Where system 10 of FIG. 1 is to be used to measure the wall and axial curvature of an elongated member 12 which is hollow, member 12 should be completely filled with a coupling medium 36 to permit the pulse energy generated by each of transducers 14–16 to propagate to the furthest external wall surface 39 of member 12 and be reflected back therefrom to the faces 32–34 of the associated transducers 14–16, respectively. As shown in FIG. 4 for a hollow member 12, corresponding to that shown in FIG. 2 for a solid member 12, and typically for transducer 14, but also representative of transducers 15 and 16, each pulse of ultrasonic energy from transducer 14 propagates through coupling medium 36 from the face 32 of transducer 14 towards elongated member 12 along a path 50.

When the transmitted ultrasoninc pulse energy encounters the external wall surface 38 of member 12 nearest transducer 14, a first portion of the transmitted ultrasonic pulse energy is reflected back from said nearest external surface 38 of member 12 towards the face 32 of transducer 14 along a path 51, the remainder of the transmitted pulse energy continuing through member 12 along path 50. When the remaining transmitted pulse energy encounters the internal wall surface 80 of member 12 nearest transducer 14, a second portion of the remaining pulse energy is reflected back towards the face 32 of transducer 14 along a path 82, the remainder of the pulse energy continuing through the coupling medium 36 within the bore of member 12, along path 50. When the remaining transmitted pulse energy encounters the internal wall surface 83 of member 12 diametrically opposed to the internal wall surface 80 nearest transducer 14, a third portion of the remaining transmitted pulse energy is reflected back towards face 32 of transducer 14 along a path 84. The remaining ultrasonic pulse energy continues along path 50 and is reflected from the external wall surface 39 of member 12 furthest from transducer 14 back towards the face 32 of transducer 14 along path 52. Similar to that shown in FIG. 2, successive reflections occur whenever a transmitted or reflected energy pulse meets any one of wall surfaces 38, 39, 80, and 83. However, only those energy pulses pertinent for practicing the present invention are shown in FIGS. 4 and 5 and discussed herein.

Figure 5:
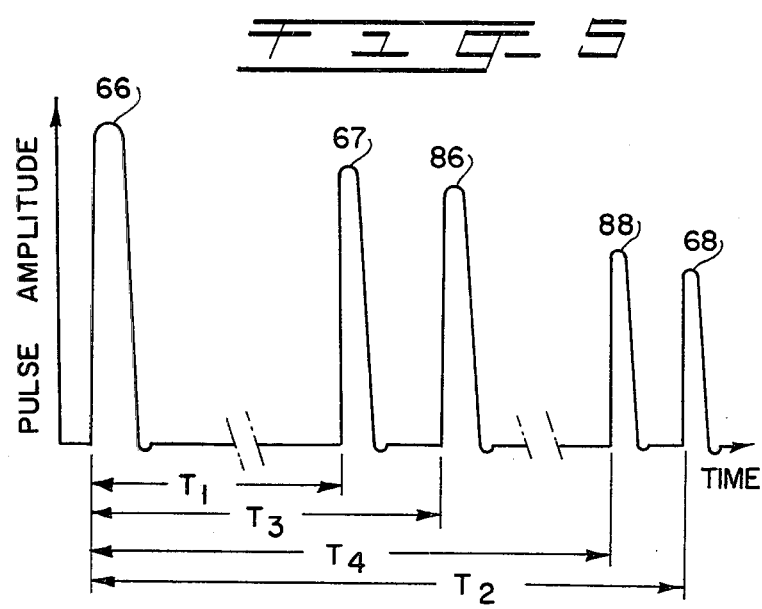
FIG. 5 is a schematic representation of an ultrasonic pulse train including reflections from wall surfaces of a hollow member filled with an acoustic medium as shown in FIG. 4.

The pulses generated by transducer 14 in FIG. 4, in response to both a pulse from transmitter 42 and the detection of pulse energy being reflected back towards transducer 14 from the wall surfaces 38, 39, 80, and 83 of member 12, if displayed on a cathode ray tube would appear as shown in FIG. 5. There, pulse 66 corresponds to the search pulse generated by transducer 14 in response to a pulse from the associated transmitter 42 over cable 46. Pulses 67 and 68, as in FIG. 3, correspond to the pulses generated by transducer 14 in response to the detection of pulse energy being reflected from the nearest and furthest diametrically opposed external wall surfaces 38 and 39, respectively, of member 12 propagating along respective paths 51 and 52. As shown in FIG. 5, the time elapsed between the generation, by transducer 14, of pulses 66 and 67, the pulses 66 and 68 are designated as time periods T1 and T2, respectively. Pulses 86 and 88 represent the pulses generated by transducer 14 in response to the detection by said transducer 14 of pulse energy being reflected from the nearest and furthest diametrically opposed internal wall surfaces 80 and 83, respectively, of member 12 propagating along respective paths 82 and 84. As shown in FIG. 5, the time elapsed between the generation, by transducer 14, of pulses 66 and 86, and pulses 66 and 88 are designated as time periods T3 and T4, respectively.

Figure 6:
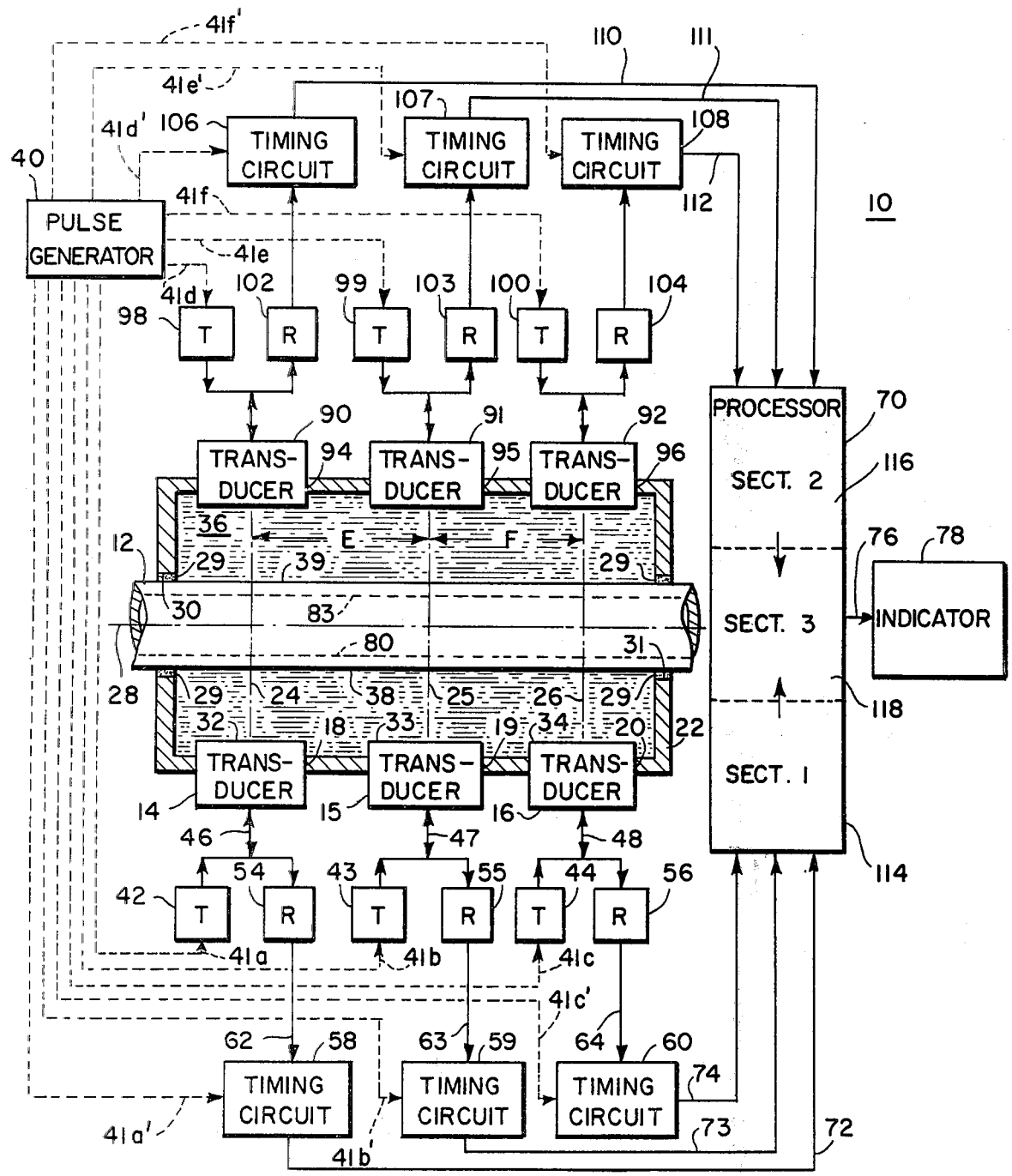
FIG. 6 is a block diagram of a nondestructive ultrasonic axial curvature measuring system embodying a second form of the present invention.

For a hollow member 12, wall and axial curvature measurements are generally performed with reference to the bore of member 12 since the internal wall surface is generally the surface of most interest. The description which follows for a hollow member 12 is mainly directed to the measurement of wall and axial curvature with reference to the internal wall surface of member 12, although it should be understood that the external wall surface could alternatively be referenced. Where curvature measurements are made with reference to the internal wall surface of member 12, each of timing circuits 58–60 need only be adapted to respond to pulses 66, 86 and 88 (FIG. 5) from each of transducers 14–16, respectively, thereby to generate an output signal representative of the time elapsed during each of periods T3 and T4. From the output signals of each of timing circuits 58–60, processor 70 can sequentially determine (a) the distance between each of the faces 32–34 of transducers 14–16, respectively, and each of the diametrically opposed internal wall surfaces 80 and 83 of member 12, (b) the deviation from straightness (h) and the radius of curvature ($R_c$) for each of said diametrically opposed internal wall surfaces 80 and 83, and (c) the axial curvature (R) of member 12 as described hereinabove.

Where the bore of a hollow member 12 is not filled with, or does not contain, a suitable acoustic coupling medium 36 and it is desired to measure the axial curvature of member 12, an alternative embodiment of the present invention as shown in FIG. 6 could be used. There, pulse generator 40, and transducers 14–16 in cooperation with the respective associated transmitters 42–44, receivers 54–56, and timing circuits 58–60 operate as described for the like-numbered components in FIG. 1. Without a coupling medium in the bore of hollow member 12, an ultrasonic energy pulse radiating from each of transducers 14–16 will only propagate along path 50 in FIG. 4 as far as internal wall surface 80 of member 12 with the reflected energy pulses returning from external wall surface 38 and internal wall surface 80 along paths 51 and 82, respectively, to the associated transducers 14–16. Timing circuits 58–60 of FIG. 6, therefore, need only be adapted to respond to the equivalent of pulses 66 and 86 of FIG. 5.

In FIG. 6, transducers 14–16 and the associated circuitry only permit a first measurement of wall curvature along the internal wall surface 80 at a first side of member 12. As described previously, a second measurement of wall curvature along the internal wall surface 83 at a second side of member 12 is necessary to determine axial curvature, where said first and second wall curvature measurements are preferably taken along diametrically opposed portions of the internal wall surface of member 12. The axial curvature of member 12 could, of course, be obtained by first measuring the internal wall curvature at said first side of member 12 using transducers 14–16 and then rotating member 12 by 180° to measure the internal wall curvature at said second side of member 12 again using transducers 14–16.

A more efficient arrangement, however, is shown in FIG. 6. There, a second set of transducers 90–92 are shown mounted in apertures 94–96, respectively, in tank 22 such that transducers 90–92 lie in the same plane defined by transducers 14–16 and the axes of transducers 90–92 lie colinear with the axes 24–26 of transducers 14–16, respectively, member 12 being positioned therebetween and surrounded by coupling medium 36. Transducers 90–92 have associated therewith respective transmitters 98–100, respective receivers 102–104, and respective timing circuits 106–108 which function as described for the corresponding components associated with transducers 14–16. Pulse generator 40 transmits pulses cyclically to both transmitters 42–46 and 98–100 over cables 41a–41c and 41d–41f, respectively, and timing circuits 58–60 and 106–108 over cables 41a'–41c' and 41d'–41f', respectively, in a manner described hereinabove for FIG. 1 thereby to permit timing circuits 58–60 and 106–108 to measure the elapsed time between the generation of a search pulse from each of respective transducers 14–16 and 94–96 and the receipt of reflected pulse energy from only the nearest one of the diametrically opposed internal wall surfaces 80 and 83.

The output signals from timing circuits 58–60 are transmitted over cables 72–74, respectively, to a first section 114 of processor 70 therein to determine the deviation from straightness and radius of curvature of internal wall surface 80. The output signals from timing circuits 106–108 are transmitted over cables 110–112, respectively, to a second section 116 of processor 70 therein to determine the deviation from straightness and radius of curvature of internal wall surface 83. The axial curvature of member 12 can then be determined in a third section 118 of processor 70 using the results obtained in the first section 114 and second section 116 of processor 70 and displayed, or recorded, on indicator 78 for the real time evaluation of the straightness of member 12.

A simplified, direct real time plot of axial curvature along member 12 can be obtained by axially moving member 12 past transducers 14–16 (FIGS. 1 and 6) and 90–92 (FIG. 6) while pulse generator 40 transmits pulses to said transducers. As a result, electrical signals representing deviation from straightness and wall curvature for each of the diametrically opposed wall surfaces 80 and 83 are generated in processor 70 which electrical signals are properly combined so as to generate a continuous output signal from processor 70 indicating the magnitude of the axial curvature component in the plane defined by the transducers. Thus, the rapidity of data taking and analysis is enhanced both by the concurrent determination of two wall curvature values and by the instantaneous and automatic processing of said two curvature values into meaningful information concerning axial curvature along member 12.

The discussion thus far assumes an absence of any effects from higher order, odd- or even-foil distortions. An odd-foil distortion is a symmetrical distortion characterized by an odd number of lobes in a tube cross section, e.g., a trifoil distortion characterized by three lobes arrayed equiangularly about the axis of the tube. An even-foil distortion is a symmetrical distortion characterized by an even number of lobes in a tube cross section.

It should be noted that even-foil distortions of any order will not substantially affect the operation of the system of FIGS. 1 and 6, since even-foil distortions will be balanced out by the averaging of values of h taken along opposed wall surfaces of member 12.

Periodic odd-foil distortions, when viewed radially from the longitudinal axis 28 of member 12, may appear initially to constitute deviations in axial curvature. Upon further observation, however, the deviation will be found to be periodic about the periphery of the tube. In some instances, these higher order odd-foil distortions may be ignored, inasmuch as they are generally much less pronounced than those caused by variations in axial curvature. Such higher order odd-foil distortions may, however, be significant in such fields as millimeter waveguide transmission, or where cylinders of a desired odd-foil geometry, e.g., triangular or pentagonal, are involved. Techniques for measuring axial curvature in a tube, with higher order odd- and even-foil effects substantially eliminated, are available through the use of a system of the type shown typically in FIG. 7 of the present invention.

An arbitrary cross section of the interior surface of hollow member 12 can be described in polar coordinates as an infinite Fourier series using the equation:

$$r(\theta) = r_o + \sum_{l=1}^{\infty} r_l \sin(l\theta + \phi_l); \qquad (5)$$

where
$r(\theta)$ is the radial distance to the waveguide surface as a function of polar angle at a given longitudinal position on elongated member 12;
$r_o$ is the nominal radius of the cross section;
$r_l$ is the magnitude of the $l^{th}$ foil distortion in the cross section; and
$\phi_l$ is the angular orientation of the $l^{th}$ foil distortion. Equation (5) can be rewritten as:

$$r(\theta) = \sum_{l=0}^{\infty} r_l \sin(l\theta + \phi_l), \qquad (6)$$

where $\phi_o = \pi/2$.

A finite-Fourier approximation, designated as $\bar{r}(\theta)$, to equation (6) can be derived from the equation:

$$\bar{r}(\theta) = \frac{a_o}{2} + \sum_{m=1}^{2M-1} a_M \cos m\theta + b_m \sin m\theta + \frac{a_M}{2} \cos M\theta, \qquad (7)$$

where
$2M$ is the number of sample points about the periphery of the cross section; and
$a_m, b_m$ are the magnitudes of the $m^{th}$ foil distortion in the ($\theta = 0$) and ($\theta = \pi/2$) directions, respectively, and can be calculated from the equations:

$$a_m = \frac{1}{M} \sum_{n=0}^{2M-1} r\left(\frac{n\pi}{M}\right) \cos\left(\frac{mn\pi}{M}\right) \qquad (8)$$

$$b_m = \frac{1}{M} \sum_{n=0}^{2M-1} r\left(\frac{n\pi}{M}\right) \sin\left(\frac{mn\pi}{M}\right) \qquad (9)$$

Figure 7:
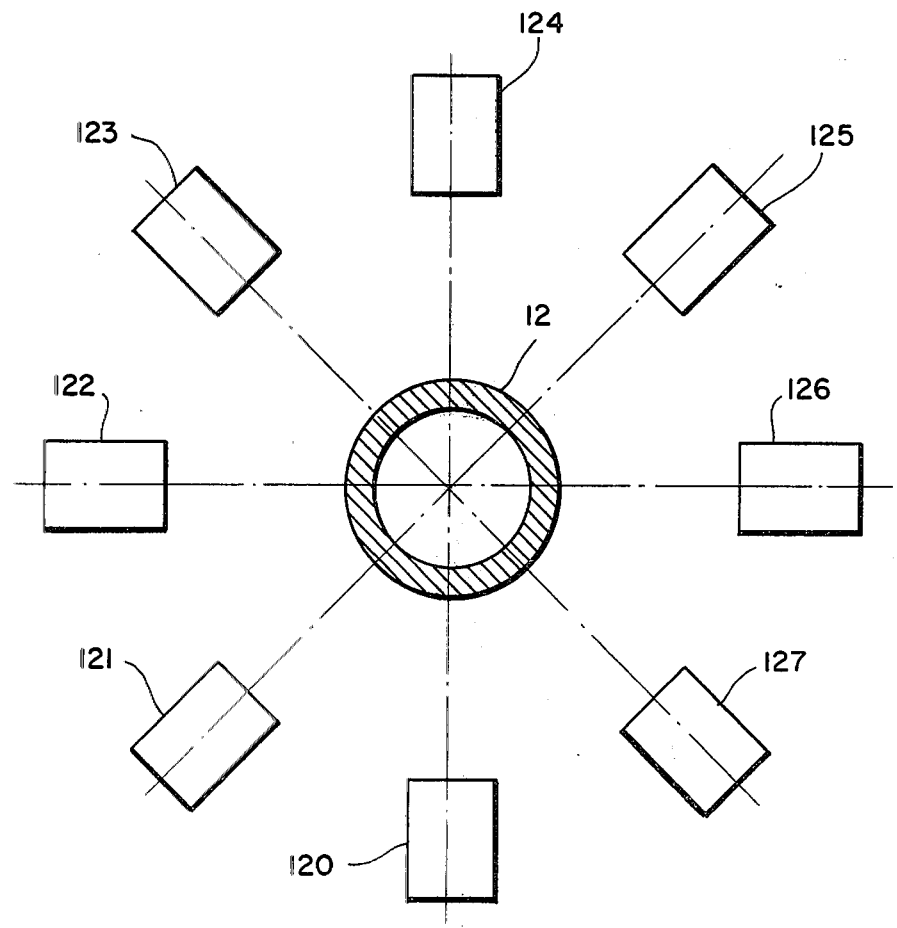
FIG. 7 is a view in side elevation of a portion of the measuring apparatus showing one transducer from each of a plurality of sets of transducers arranged about an elongated member to obtain an axial curvature measurement while eliminating the effects of up to quadrafoil distortions.

Turning to FIG. 7, there is shown one transducer from each of eight sets of three or more transducers and designated as transducers 120–127, each set of transducers being arranged in a similar manner to a set of transducers (14–16 or 90–92) shown in FIGS. 1 and 6. Transducers 120–127 are equiangularly arrayed around the outer periphery of member 12 at a predetermined distance from said member to define a plane which is approximately normal to the longitudinal axis 28 of member 12. Other methods of determining axial curvature are also available where transducers 120–127 need not be equiangularly arrayed about member 12. However, where the transducers are not equiangularly arrayed, equations (5)–(9) above should be modified to account for transducer positions as is well known in the art. Each of transducers 120–117 associated therewith a transmitter, receiver, and timing circuit similar to that shown for each transducer in FIGS. 1 and 6 which are connected to a processor 70. Processor 70, in accordance with the principles of equations (5)–(9) instead of equations (2)–(4), can derive the arbitrary cross section of the interior surface of member 12 in the plane of transducers 120–127 and also determine the location of the longitudinal axis 28 of member 12 in said cross section. Processor 70 would also determine the cross-sectional configuration and location of the longitudinal axis 28 within said configuration in the plane of the other corresponding transducers in each of the sets of transducers. From the determined polar coordinates of the longitudinal axis 28 of member 12 in each of the said planes, processor 70 could, by well-known mathematical techniques, determine the magnitude and direction of the axial curvature of member 12.

By using eight transducers in each plane, it is only possible to obtain Fourier components up to quadrafoil distortions as indicated by the elements of equation (7). Therefore, FIG. 7 merely illustrates a typical arrangement for measuring axial curvature of a member 12 where the effects of higher odd- and even-foil distortions are to be compensated for. For foil distortions above quadrafoil, the amount of transducers arrayed about member 12 would have to be increased appropriately.

What is claimed is:

1. A method for measuring the axial curvature of an elongated member by ultrasonic pulse-echo techniques, the method comprising the steps of:
   a. transmitting an ultrasonic search signal towards and approximately normal to the longitudinal axis of said elongated member from each of a plurality of transducer sites, said sites being arrayed about and nominally equidistant from said longitudinal axis in at least three parallel planes spaced therealong;
   b. receiving at each of said sites a portion of the transmitted search signal reflected back thereto from at least one of a first associated point and a second associated point diametrically opposed to said first point on a wall surface of said elongated member;
   c. generating first electrical signals in response to receipt of the reflected portions of the search signals which are representative of the respective distances between each site and at least one of said first and second diametrically opposed points on said wall surface of said elongated member; and
   d. sequentially generating a second electrical signal in response to said first electrical signals describing in polar coordinates the location of the longitudinal axis of said elongated member in each of said three parallel planes, and generating a third electrical signal in response to said second electrical signal which defines the magnitude and direction of the axial curvature of said member.

2. Apparatus for measuring the deviation from straightness between two points along a surface of a member by ultrasonic pulse-echo techniques, the apparatus comprising:
   at least three transducer means arranged normal to said surface and respectively opposite said two points and at least one point intermediate said two points, said transducer means being further arranged nominally equidistant from said surface and at predetermined distances from one another to define a plane which approximately includes the longitudinal axis of said member;
   first means adapted to hold an acoustic coupling medium between and in contact with each transducer means and the wall surface of said member nearest each transducer means;
   second means for generating first electrical signals capable of being converted into ultrasonic search signals by said transducer means and transmitted via said first means to said member;
   third means connected to each of said transducer means for generating second electrical signals indicating the time elapsed between the transmission of said ultrasonic search signals and the detection by each of said transducer means of a portion of the search signal reflected from the point on said surface opposite thereto; and
   processor means for generating a third electrical signal in response to said second electrical signals indicative of the deviation from straightness of said surface between said two points.

3. Apparatus for measuring the axial curvature of an elongated member having a longitudinal axis by ultrasonic pulse-echo techniques, the apparatus comprising:
   a plurality of ultrasonic transducer means arranged in at least three sets, each set having at least three transducer means, each of said transducer means being arranged nominally equidistant from and normal to said longitudinal axis, the corresponding transducer means from each set of transducer means being arrayed about said longitudinal axis to define a separate plane which is normal to said longitudinal axis;
   first means for generating first electrical signals capable of being converted into ultrasonic search signals by said transducer means and transmitted to said elongated member;
   second means connected to each of said transducer means for generating second electrical signals indicating the time elapsed between the transmission of said ultrasonic search signals and the detection by each of said transducer means of a portion of the search signal reflected back towards each of said transducer means from a point opposite thereto and on at least one of an external and internal wall surface of said elongated member; and
   processor means connected to said second means for sequentially generating in response to said second electrical signals, third electrical signals describing in polar coordinates the location of the longitudinal axis of said member in each of the separate planes defined by the corresponding transducer means in said sets of transducer means, and generating a fourth electrical signal in response to said third electrical signals indicative of the magnitude and direction of the axial curvature of said member.

4. A method of measuring the axial curvature of a nominally straight elongated member having a first surface and a second surface, the first and second surfaces being substantially symmetrical about a longitudinal axis; which comprises:
   a. positioning the member with respect to three sites spaced at predetermined distances along a line substantially parallel to the longitudinal axis, each site being capable of transmitting and receiving ultrasonic signals along a path substantially normal to the first and second surfaces, the paths and the longitudinal axis lying substantially in a first plane;
   b. at each site, transmitting ultrasonic signals to the first and second surfaces and receiving portions of the ultrasonic signals reflected from the first and second surfaces;
   c. generating first electrical signals representing the transit times of the portions of the ultrasonic signals reflected from the first surface;
   d. generating a second electrical signal from the first electrical signals, the second electrical signal indicating the curvature of the first surface in the first plane;
   e. generating third electrical signals representing the transit times of the portions of the ultrasonic signals reflected from the second surface;
   f. generating a fourth electrical signal from the third electrical signal, the fourth electrical signal indicating the curvature of the second surface in the first plane; and
   g. generating a fifth electrical signal from the second and fourth electrical signals, the fifth electrical signal indicating the axial curvature of the member in the first plane.

5. The method of claim 4, which further comprises:
   h. performing steps (a)–(g) for an additional three sites, the paths from the additional three sites and the longitudinal axis lying substantially in a second plane perpendicular to the first plane; and
   i. generating a sixth electrical signal from the fifth electrical signal generated in step (g) for the three sites and the fifth electrical signal generated in step (g) for the additional three sites; the sixth electrical signal indicating the net axial curvature of the member.

6. The method of claim 4 wherein the member is hollow and the first and second surfaces are interior surfaces.

7. Apparatus for measuring the axial curvature of a nominally straight elongated member having a first surface and a second surface, the first and second surfaces being substantially symmetrical about a longitudinal axis, which comprises:
   a. three transducers spaced at predetermined distances along a line substantially parallel to the longitudinal axis, each transducer being capable of transmitting ultrasonic signals along a path substantially normal to the first and second surfaces and receiving portions of the ultrasonic signals reflected along the paths by the first and second surfaces, the paths and the longitudinal axis lying substantially in a plane;
   b. means connected to each transducer for generating first electrical signals capable of being converted into ultrasonic signals by the transducers;
   c. means connected to each transducer for generating second electrical signals representing the transit times of the portions of the ultrasonic signals reflected from the first surface and third electrical signals representing the transit times of the portions of the ultrasonic signals reflected from the second surface; and
   d. means for generating fourth, fifth, and sixth electrical signals, the fourth electrical signal being generated from the second electrical signals and indicating the curvature of the first surface in the plane, the fifth electrical signal being generated from the third electrical signals and indicating the curvature of the second surface in the plane, and the sixth electrical signal being generated from the fourth and fifth electrical signals and indicating the axial curvature of the member in the plane.

8. The apparatus of claim 7 wherein the elongated member is hollow and is filled with an acoustic coupling medium, and the first and second surfaces are interior surfaces.

9. The apparatus of claim 7 wherein the elongated member is hollow and the first and second surfaces are interior surfaces.

10. Apparatus for measuring the axial curvature of a nominally straight, elongated member having a first surface and a second surface, the first and second surfaces being symmetrical about a longitudinal axis, which comprises:
   a. three first transducers spaced at predetermined distances along a first line substantially parallel to the longitudinal axis, the first transducers being capable of transmitting ultrasonic signals along first paths substantially normal to the first surface and receiving portions of the ultrasonic signals reflected from the first surface, the first paths and the longitudinal axis lying substantially in a plane;
   b. three second transducers spaced at predetermined distances along a second line substantially parallel to the longitudinal axis and diametrically opposite the first line, the second transducers being capable of transmitting ultrasonic signals along second paths substantially normal to the second surface and receiving portions of the ultrasonic signals reflected from the second surface, the second paths lying substantially in the same plane as the longitudinal axis;
   c. means connected to each transducer for generating first electrical signals capable of being converted into ultrasonic signals by the transducers;
   d. means connected to each first transducer for generating second electrical signals representing the transit times of the portions of the ultrasonic signals reflected from the first surface;
   e. means connected to each second transducer for generating third electrical signals representing the transit times of the portions of the ultrasonic signals reflected from the second surface; and
   f. means for generating fourth, fifth and sixth electrical signals, the fourth electrical signal being generated from the second electrical signals and indicating the curvature of the first surface in the plane, the fifth electrical signal being generated from the third electrical signals and indicating the curvature of the second surface in the plane, and the sixth electrical signal being generated from the fourth and fifth electrical signals and indicating the axial curvature of the member in the plane.

* * * * *